United States Patent [19]
Chaykin

[11] Patent Number: 6,007,809
[45] Date of Patent: Dec. 28, 1999

[54] METHOD AND PRODUCT FOR ELIMINATING UNDESIRABLE SIDE EFFECTS OF EATING VEGETABLES SUCH AS ONION OR GARLIC

[76] Inventor: Sterling Chaykin, 1027 Maple La., Davis, Calif. 95616

[21] Appl. No.: 08/062,494

[22] Filed: May 13, 1993

Related U.S. Application Data

[63] Continuation of application No. 07/984,285, Dec. 1, 1992, abandoned, which is a continuation of application No. 07/865,810, Apr. 7, 1992, abandoned, which is a continuation of application No. 07/574,653, Aug. 29, 1990, abandoned.

[51] Int. Cl.[6] ............................................. C12N 1/18
[52] U.S. Cl. ............................................. 424/93.51
[58] Field of Search .................... 424/93 S, 50, 424/475, 93.51; 435/256; 514/974

[56] References Cited

U.S. PATENT DOCUMENTS

| | | | |
|---|---|---|---|
| 1,729,752 | 10/1929 | Southgate | 424/93 |
| 4,079,124 | 3/1978 | Sipos | 424/32 |
| 4,079,125 | 3/1978 | Sipos | 424/32 |
| 4,719,114 | 1/1988 | Percel | 435/256 |
| 4,960,591 | 10/1990 | Gribou | 424/93 |
| 5,003,098 | 3/1991 | Sirens et al. | 514/970 |

FOREIGN PATENT DOCUMENTS

| | | | |
|---|---|---|---|
| 2096887 | 7/1970 | France | 424/93 |
| 2096887 | 3/1972 | France | 424/93 |
| 3738599 | 5/1989 | Germany | 435/256 |
| 8303102 | 9/1983 | WIPO . | |

Primary Examiner—Jean C. Witz
Attorney, Agent, or Firm—Richard Aron Osman

[57] ABSTRACT

A method for reducing the undesirable side effects normally resulting from eating certain vegetables. Specifically, the malodorous breath and perspiration from eating garlic, onion, etc. and the burping and flatulence resulting from eating cucumber, beans, etc., can be avoided by ingesting active dry yeast protected by an enteric coating.

20 Claims, No Drawings

METHOD AND PRODUCT FOR ELIMINATING UNDESIRABLE SIDE EFFECTS OF EATING VEGETABLES SUCH AS ONION OR GARLIC

This is a continuation of application Ser. No. 07/984,285 filed Dec. 1, 1992 now abandoned, which is a continuation of Ser. No. 07/865,810, filed Apr. 7, 1992, now abandoned, which is a continuation of Ser. No. 07/574,653 filed Aug. 29, 1990 now abandoned.

BACKGROUND OF THE INVENTION

The present invention relates to a method of reducing undesirable side effects of eating certain vegetables (e.g. onion and garlic).

A person eating certain vegetables, such as onion and garlic, typically exhibits malodorous breath and perspiration within a few hours. The digestion of these and other vegetables such as cabbage, cucumber, radish and beans can lead to digestive distress, including burping and flatulence. The malodorous breath and perspiration tend to be caused by sulfur-containing compounds, such as dimethylsulfide, methymercaptan, and hydrogen sulfide. Intestinal distress results from a buildup of these and other gases (including carbon dioxide and methane) in the intestine. The escape of intestinal gases produces burping and flatulence. The passage of such sulfur-containing compounds across the intestinal wall and into the blood stream causes them to be exhaled through the lungs and secreted as sweat, saliva and other bodily fluids.

A variety of techniques have been used for alleviating certain of the undesirable side effects. In general, these techniques are cosmetic and involve masking malodors and other aromas, or removing them from the mouth through chemistry, for example, chlorophyll-containing products. Further, intestinal gas buildup is minimized by facilitating the elimination of microbubbles. These approaches do no change the underlying digestive processes.

U.S. Pat. No. 4,634,588 discloses that the residue produced by the removal of water and alcohol from wine or from the alcohol extract of fermentation residue will alleviate the side effects of malodors including that of garlic. The extraction procedures are so harsh that if active enzymes or live yeast were present, their activity would have been severely diminished or destroyed. Moreover, if live yeast or yeast enzymes were present, they would be unprotected from the acidity and proteolytic activity of the stomach and anterior intestine (i.e. the first portions of the duodenum where the stomach acids have not yet been neutralized by the basic secretions of the pancreas).

A grape juice has been sold which ferments at a pH of about 3.2 to 3.6 to produce some wine yeast growth. However, such product, if unprotected, would pass through the stomach to the mid and posterior intestine in an inactive form.

Also, various forms of yeast have been sold as a dietary supplement. For example, brewer's yeast has been sold for that purpose in health food stores. However, it is processed under adverse conditions (e.g. alkaline washing, solvent extractions, and drying conditions) which render it unprotected from the acidity and proteolytic activity of the stomach and anterior intestine, causing inactivity. (Gerald Reed and Henry J. Peppler, *Yeast Technology,* Westport, Conn., Avi Publishing co., Inc., 1973; in particular, Chapters 5 and 11 and references contained therein).

SUMMARY OF THE INVENTION

In accordance with the present invention, it is found that active yeast may be employed to reduce or eliminate the foregoing undesirable side effects. Specifically, when a person eating the vegetables ingests dry active yeast in a form which retains substantial enzymatic activity under conditions present in the stomach and intestinal tract, in sufficient quantities, it will significantly reduce or eliminate the undesirable side effects normally resulting from eating the vegetables. In a preferred embodiment, the active yeast is in dry form and protected by an enteric coating.

DETAILED DESCRIPTION OF PREFERRED EMBODIMENTS

As used herein, the term "dry active yeast" refers to a viable dry active yeast containing the desired enzymes or a yeast product which is not viable but which contains yeast enzymes in active form. The activity is measured by the ability of the yeast enzymes to significantly reduce or eliminate the side effects of eating certain vegetables. Specifically, such activity is sufficient to significantly reduce or eliminate the malodorous effects on breath, perspiration and saliva from eating garlic or onion.

As used herein, "activity" means the ability to provide the foregoing benefits to an adult of average weight who ingests 30 grams of green onion and 15 grams of garlic by using 0.5 grams of the yeast in dry form. The activity is also sufficient to significantly reduce or eliminate the digestive tract discomfort side effect (including gas pain, burping and flatulence) caused by ingesting garlic, onion, cabbage, cucumber, radish or beans.

As used herein, "onion" means the onion family including green onions, fresh or dried onions, leaks and chives.

As used herein, "cabbage" means the cabbage family including cabbage, brussel sprouts, cauliflower and broccoli.

The activity of the yeast is expressed after the yeast has passed the acidity and proteolytic conditions of the stomach and anterior intestine. This is because the yeast enzymes are believed to perform during normal digestion by redirecting the digestive fates of the parent compounds from which the malodors and other undesirable digestive gases come, converting these parent compounds, which originate in the vegetables cited above, to compounds other than malodors and other undesirable digestive gases.

There are a number of factors which are important in determining the activity of the dry yeast. They include the yeast growing conditions, the yeast harvesting and drying conditions, the appropriate strain of yeast, and the presence of an enteric coating.

The conditions of drying and extraction must be such as not to inactivate the yeast or enzymes contained therein. In that regard, the active dry yeast typically has a moisture content in the range 7.5–8.3% water and should not have been exposed to a temperature in excess of about 45° C. In contrast, brewer's yeast sold in health food stores as a diet supplement typically is processed under substantially more adverse conditions. It has been determined that such yeast, without a protective coating, would be inadequately protected to survive the conditions of the stomach and anterior intestine.

Although not essential, it is preferable for the yeast to have been grown under conditions which will survive the low pH of the stomach and anterior intestine. In that regard, the preferred yeast would be grown at a pH of no greater than about 3.2. Otherwise, it may be necessary to provide an enteric coating.

The most effective type of yeast, generically called a wine yeast, is sold under the strain designations "Montrachet" and "Pasteur Champagne" yeast, suitably supplied by Universal Foods under the designation "Active Dry". So long as this yeast is not subjected to temperatures substantially in excess of room temperature, and/or in the presence of oxygen and/or excess humidity for long periods, it has been found to survive the conditions of the stomach and anterior intestine so as to be effective even without an enteric coating.

Active dry baker's yeast is another suitable form of yeast. Preferably it should be coated by an enteric coating for protection from the harsh conditions of the stomach and anterior intestine. Suitable baker's yeast is sold under the designation Active Dry by Universal Foods and Fleisman.

Brewer's yeast is also an effective form of active dry yeast. It, too, can be effective without an enteric coating.

The preferred form of the active dry yeast product of the present invention is one which is enterically coated. This allows for a wide variety of yeast strains which will remain active on passage through the stomach and anterior intestine. Any of the known enteric coatings may be used in accordance with the present invention. Specifically, such coatings should be capable of protecting the yeast during passage through the stomach and anterior intestine and releasing the yeast on passage through the mid and posterior intestine. Suitable enteric coatings are disclosed in International Encyclopedia of Pharmacology and Therapeutics, §39B, "Pharmacology of Intestinal Absorption of Drugs", Vol. 1, W. Forth and W. Rummel (Editors), Pergamon Press, New York, 1975, p.385–6. Suitable coatings include vegetable oil, mineral oil, waxes, esters, polymers, pH dependent coatings and pharmaceutical shellacs.

Other forms of the active dry yeast may also be employed, particularly of the wine yeast type. Thus, the product could be sprinkled in a powder onto the food, or compacted into the form of a pill, packed into a gelatin capsule, or formed into a caplet, tablet or lozenge. In addition, the yeast can be formulated into candy or other edible material, so long as it is in a form which survives the conditions of the stomach and anterior intestine.

The dosage of the yeast depends upon the quantity of vegetable consumed with the corresponding malodor and digestive distress potential of the meal, together with the digestive characteristics of the subject. For example, wine yeast (active dry Pasteur Champagne yeast) at a dosage of at least about 0.5 grams will protect against the malodorous and digestive tract distress potential of 30 grams of green onions and 15 grams of garlic, both consumed in the same meal. Similarly, the same yeast at a dosage of 1.0 grams will protect against the digestive distress potential of 150 grams of baked beans, 200 grams of cucumbers, 200 grams of cabbage, all consumed at the same meal. A suitable dosage range of active dry yeast is at least about 0.25 grams, on the order of 0.25 to 5.0 grams per meal and, preferably, 0.5 to 1.0 grams. The timing of consumption of the dry active yeast product of the present invention is preferably during the course of the meal or slightly before, say within one hour. Moreover, it could be taken a short time after completing the meal, e.g. within 15 minutes.

What is claimed is:

1. A method for reducing or eliminating a malodorous effect on breath from eating a vegetable selected from the group consisting of garlic, onion, and radish, said method comprising the steps of eating at least one of said vegetables and ingesting active dry yeast, wherein said ingested active yeast has been selected for survival under acidic conditions or has been enteric coated and said ingested active yeast is in an effective dosage to significantly reduce or eliminate said malodorous effect.

2. The method of claim 1 in which, during ingestion, said active yeast is in dry form and protected by an enteric coating capable of protecting the yeast on passage through the stomach and anterior intestine and of releasing said active yeast on passage through the remaining portions of the intestine.

3. The method of claim 2 in which said enteric coating is selected from the group consisting of vegetable oil, mineral oil, waxes, esters, polymers, pH dependent coatings, and pharmaceutical shellacs.

4. The method of claim 1 in which said active dry yeast was formed by growing yeast at a pH lower than 3.2.

5. The method of claim 1 in which said active dry yeast is selected from the group consisting of baker's yeast, brewer's yeast and wine yeast.

6. The method of claim 1 in which said active dry yeast has not been subjected to treatments which would destroy its enzyme activity.

7. The method of claim 1 in which said active dry yeast is contained in a vehicle selected from the group consisting of a pill, gelatin capsule, caplet, tablet, lozenge, candy or gum.

8. The method of claim 1 in which said active dry yeast is ingested at a dosage of at least 0.5 gm/meal.

9. A method for reducing or eliminating intestinal discomfort from eating a vegetable selected from the group consisting of garlic, onion, cabbage, cucumber, radish and beans, said method comprising the steps of eating at least one of said vegetables and ingesting active dry yeast, wherein said ingested active yeast has been selected for survival under acidic conditions or has been enteric coated and said ingested active yeast is in an effective dosage to significantly reduce or eliminate said intestinal discomfort.

10. The method of claim 9 in which, during ingestion, said active yeast is in dry form and protected by an enteric coating capable of protecting the yeast on passage through the stomach and anterior intestine and of releasing said active yeast on passage through the remaining portions of the intestine.

11. The method of claim 10 in which, said enteric coating is selected from the group consisting of vegetable oil, mineral oil, waxes, esters, polymers, pH dependent coatings, and pharmaceutical shellacs.

12. The method of claim 9 in which said active dry yeast was formed by growing yeast at a pH lower than 3.2.

13. The method of claim 9 in which said active dry yeast is selected from the group consisting of baker's yeast, brewer's yeast and wine yeast.

14. The method of claim 9 in which said active dry yeast has not been subjected to treatments which would destroy its enzyme activity.

15. The method of claim 9 in which said active dry yeast is contained in a vehicle selected from the group consisting of a pill, gelatin capsule, caplet, tablet, lozenge, candy or gum.

16. The method of claim 9 in which said active dry yeast is ingested at a dosage of at least 0.5 gm/meal.

17. The method of claim 9 in which said intestinal discomfort results from excess intestinal gas.

18. The method of claim 1 in which said active dry yeast has been selected for survival under acidic conditions by having been grown at a pH of or lower than 3.2.

19. The method of claim 1 in which said active dry yeast is Pasteur Champagne yeast.

20. The method of claim 1 in which said Pasteur Champagne yeast is without an enteric coating.

* * * * *